(12) United States Patent
De Vries et al.

(10) Patent No.: US 9,962,104 B2
(45) Date of Patent: May 8, 2018

(54) STRESS-MEASURING DEVICE AND METHOD

(75) Inventors: Jan Johannes Gerardus De Vries, Eindhoven (NL); Martin Ouwerkerk, Culemborg (NL)

(73) Assignee: Koninklijke Philips N.V., Eindhoven (NL)

( * ) Notice: Subject to any disclaimer, the term of this patent is extended or adjusted under 35 U.S.C. 154(b) by 759 days.

(21) Appl. No.: 14/110,454

(22) PCT Filed: Apr. 2, 2012

(86) PCT No.: PCT/IB2012/051592
§ 371 (c)(1),
(2), (4) Date: Oct. 8, 2013

(87) PCT Pub. No.: WO2012/140537
PCT Pub. Date: Oct. 18, 2012

(65) Prior Publication Data
US 2014/0031704 A1    Jan. 30, 2014

(30) Foreign Application Priority Data
Apr. 14, 2011   (EP) ..................................... 11162418

(51) Int. Cl.
*A61B 5/053*    (2006.01)
*A61B 5/16*    (2006.01)
(Continued)

(52) U.S. Cl.
CPC ............ *A61B 5/0531* (2013.01); *A61B 5/021* (2013.01); *A61B 5/0533* (2013.01); *A61B 5/165* (2013.01);
(Continued)

(58) Field of Classification Search
None
See application file for complete search history.

(56) References Cited

U.S. PATENT DOCUMENTS 5,064,410 A * 11/1991 Frenkel ................ A61B 5/0531
600/26
5,421,344 A    6/1995 Popp
(Continued)

FOREIGN PATENT DOCUMENTS

CN    101032395 A    9/2007
EP    1407713 A1    4/2004
(Continued)

OTHER PUBLICATIONS

Storm, H., et al "Skin conductance correlates with perioperative stress." (2002) Acta Anaesthesiologica Scandinavica, 46.7, 887-895.*

(Continued)

*Primary Examiner* — Jacqueline Cheng
*Assistant Examiner* — Jairo Portillo

(57) ABSTRACT

A stress-measuring device (10) and method determines a level (15) of stress of a user (1), in particular long-term stress. The stress-measuring device (10) includes an input interface (12) for receiving a skin conductance signal (11) indicating the skin conductance of the user (1), the skin conductance signal (11) over time forming skin conductance trace data (13). The stress-measuring device (10) further includes a processing unit (14) for processing the skin conductance trace data (13). The processing unit (14) determines, over at least a portion of the skin conductance trace data (13), values of a rise time (tr) between at least two different points of the skin conductance trace data (13), a frequency distribution of the rise time (tr) values, and the level (15) of stress of the user (1) based on the determined frequency distribution.

18 Claims, 7 Drawing Sheets

(51) Int. Cl.
*A61B 5/00* (2006.01)
*A61B 5/021* (2006.01)
*A61B 5/0205* (2006.01)
*A61B 5/024* (2006.01)

(52) U.S. Cl.
CPC ............ *A61B 5/681* (2013.01); *A61B 5/6802* (2013.01); *A61B 5/72* (2013.01); *A61B 5/7235* (2013.01); *A61B 5/02055* (2013.01); *A61B 5/02405* (2013.01); *A61B 5/6831* (2013.01)

(56) References Cited

U.S. PATENT DOCUMENTS

| | | | | |
|---|---|---|---|---|
| 6,091,973 | A | * | 7/2000 | Colla .................. A61B 5/0205 600/324 |
| 6,482,163 | B2 | * | 11/2002 | Oka ................... A61B 5/14539 600/300 |
| 6,571,124 | B1 | * | 5/2003 | Storm .................. A61B 5/0531 600/300 |
| 7,547,279 | B2 | | 6/2009 | Kim et al. |
| 8,463,372 | B2 | | 6/2013 | Storm |
| 8,882,669 | B2 | | 11/2014 | Westerink et al. |
| 2004/0039418 | A1 | * | 2/2004 | Elstrom ............... A61B 5/0048 607/3 |
| 2004/0117212 | A1 | * | 6/2004 | Kong .................... G06Q 50/22 705/2 |
| 2005/0154264 | A1 | | 7/2005 | Lecompte |
| 2005/0154269 | A1 | | 7/2005 | Lecompte et al. |
| 2006/0142968 | A1 | * | 6/2006 | Han ..................... A61B 5/0205 702/120 |
| 2009/0076341 | A1 | | 3/2009 | Kristofer et al. |
| 2009/0270170 | A1 | | 10/2009 | Patton |
| 2010/0004977 | A1 | * | 1/2010 | Marci .................... G06Q 10/10 705/7.32 |
| 2010/0022852 | A1 | | 1/2010 | Westerink et al. |

FOREIGN PATENT DOCUMENTS

| | | |
|---|---|---|
| JP | S57183831 A | 11/1982 |
| JP | 09019420 A | 7/1995 |
| JP | H09135826 A | 5/1997 |
| JP | 0071537 B2 | 4/2008 |
| JP | 2008302127 A | 12/2008 |
| WO | 0154043 A1 | 7/2001 |
| WO | 200154043 A1 | 7/2001 |
| WO | 2008099320 A1 | 8/2008 |
| WO | 2010107788 A2 | 9/2010 |

OTHER PUBLICATIONS

Perry, John Christian. The psychophysiology of risk processing and decision making at a regional stock exchange (2007) Diss. Massachusetts Institute of Technology, 1-215.*
Lim et al: "Decomposing Skin Conductance Into Tonic and Phasic Components"; International Journal of Psychophysiology, 25, 1997, pp. 97-109.
Schumm et al: "Effect of Movements on the Electrodermal Response After a Startle Event"; IEEE, Pervasive Computing Technologies for Healthcare, PervasiveHealth 2008, pp. 315-318.
Poh et al: "A Wearable Sensor for Unobtrusive, Long-Term Assessment of Electrodermal Activity"; IEEE Transactions on Biomedical Engineering, vol. 57, No. 5, May 2010 pp. 1243-1252.
Setz et al: "Discriminating Stress From Cognitive Load Using a Wearable EDA Device"; IEEE Transactions on Information Technology in Biomedicine, vol. 14, No. 2, Mar. 2010, pp. 410-417.
McEwen: "Central Effects of Stress Hormones in Health and Disease:Understanding the Protective and Damaging Effects of Stress and Stress Overload"; Eur. J. Pharmoacol. Apr. 7, 2008, vol. 583, (2-3), pp. 174-185.
Scrgauge, "A computer program for the detection and quantification of SCRs", Kolish P. Electrodermal Activity, PLENUM, pp. 432-442.

* cited by examiner

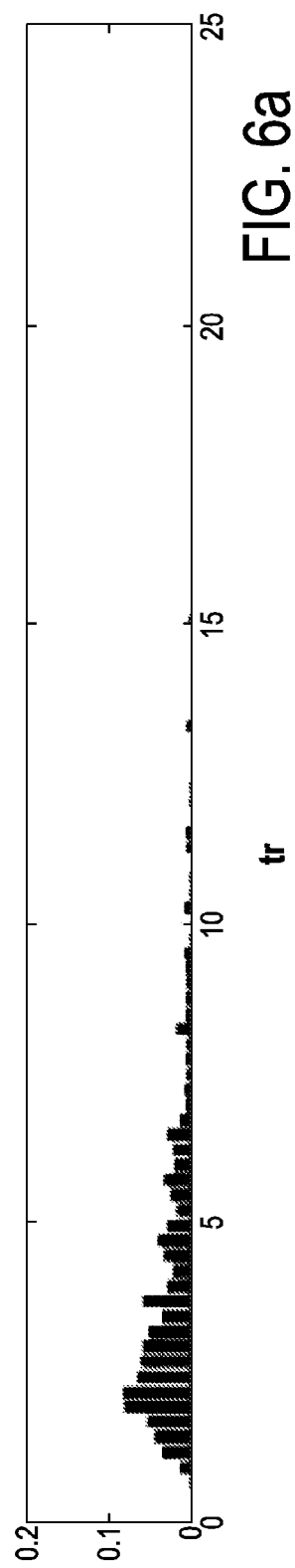
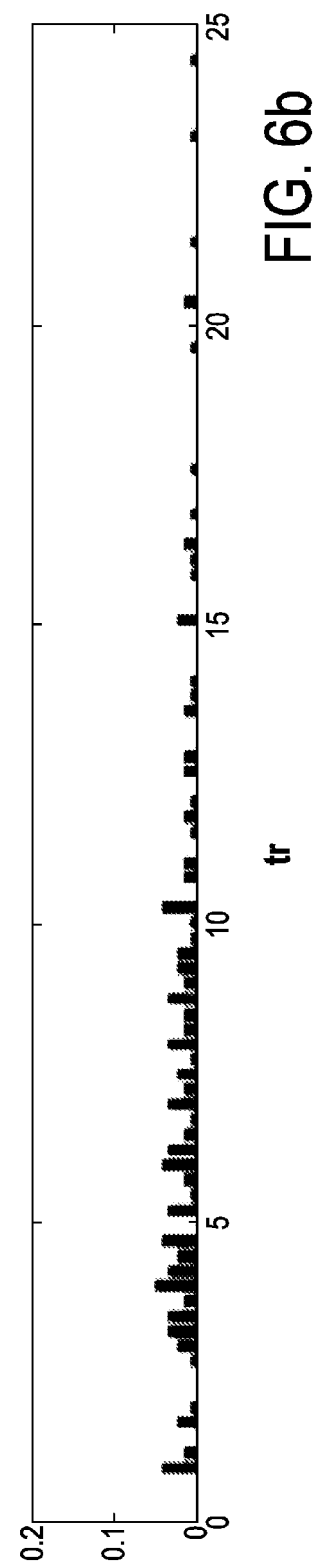
FIG. 6a
FIG. 6b

STRESS-MEASURING DEVICE AND METHOD

CROSS-REFERENCE TO PRIOR APPLICATIONS

This application is the U.S. National Phase application under 35 U.S.C. § 371 of International Application No. PCT/IB2012/051592, filed on Apr. 2, 2012, which claims the benefit of European Patent Application No. 11162418.5, filed on Apr. 14, 2011. These applications are hereby incorporated by reference herein.

FIELD OF THE INVENTION

The present invention relates to a stress-measuring device and method for determining a level of stress of a user, in particular long-term stress. The present invention also relates to a wearable device and a stress-measuring system, each comprising such stress-measuring device. Further, the present invention relates to a computer program implementing such stress-measuring method.

BACKGROUND OF THE INVENTION

Skin conductance is known as a measure for short-term effective reactions, such as emotions. In this sense, skin conductance is typically analyzed using the phasic component of the skin conductance signal, having rises and falls of duration in the order of seconds.

For example the article "Effect of movements on the electrodermal response after a startle event" by J. Schumm, M. Bachlin, C. Setz, B. Arnrich, D. Roggen and G. Tröster, Second International Conference on Pervasive Computing Technologies for Healthcare, 2008, pages 315-318, discloses an electrodermal activity (EDA) sensor that measures the EDA at the fingers via finger straps, performs signal processing of the EDA and simultaneously measures the acceleration of the fingers. The effect of continuous, stationary movements on the EDA is presented. Controlled speeds of walking as movements and startle events as an actuator are performed. The EDA is investigated by measuring the conductivity of the skin. The signal consists of a tonic component and a fast-changing phasic component superposed on the tonic component. The startle event leads to peak-shaped responses in the phasic part of the signal. A simple peak-detection algorithm with a threshold is applied to the phasic signal. A similar device is also described in the article "Discriminating Stress From Cognitive Load Using a Wearable EDA Device" by C. Setz, B. Arnich, J. Schumm, R. La Marca, G. Tröster, U. Ehlert, IEEE Transactions on Information Technology in Biomedicine, Vol. 14, No. 2, March 2010, pages 410-417.

When considering the determination of a stress level from a physiological signal, it is important to discriminate between short-term stress and long-term stress. Short-term stress is usually conceptualized in terms of startle responses or events, i.e. the user faces a changed context and the user's body acts quickly to adapt to the new context situation, resulting in a change of a physiological signal. Long-term stress occurs when short-term stress happens too often, without sufficient possibility to recover from it. The effects build up, causing more bodily processes to change or be disturbed, resulting possibly in illnesses because of a weaker immune system, burn-out syndrome and the like.

For example, in "Central effects of stress hormones in health and disease: Understanding the protective and damaging effects of stress and mediators", B. McEwen, European Journal on Pharmacology 583, 2008, pages 174-185, it is disclosed that, on the one hand, acute stress (short-term) responses promote adaptation and survival via responses of neural, cardiovascular, autonomic, immune and metabolic systems, and, on the other hand, chronic (long-term) stress can promote and exacerbate pathophysiology through the same systems that are dysregulated. The burden of chronic (long-term) stress and accompanying changes in personal behaviors is called allostatic overload.

The general problem with physiological signals is a good interpretation of these signals. Generally, the context situation in which the physiological signal was measured must be known.

SUMMARY OF THE INVENTION

It is an object of the present invention to provide a (long-term) stress-measuring device and method for determining a level of stress of a user, in particular long-term stress, which provides a context situation independent detection of the stress level. It is also an objective of the present invention to provide such a stress-measuring device and method which is less obtrusive and/or less expensive. Further, it is an object of the present invention to provide a wearable device comprising such stress-measuring device, a stress-measuring system, comprising such stress-measuring device and a computer program implementing such stress-measuring method.

In a first aspect of the present invention, a stress-measuring device is presented for determining a level of stress of a user, in particular long-term stress, the device comprising an input interface for receiving a skin conductance signal indicating the skin conductance of the user, the skin conductance signal over time forming skin conductance trace data. The device further comprises a processing unit for processing the skin conductance trace data, the processing unit adapted to determine, over at least a portion of the skin conductance trace data, values of a rise time between at least two different (time) points of the skin conductance trace data, to determine a frequency distribution of the rise time values, and to determine the level of stress of the user, in particular long-term stress, based on the determined frequency distribution.

In a further aspect of the present invention a device wearable by a user is presented, the wearable device comprising the stress-measuring device, and a skin conductance sensor for sensing the skin conductance of the user.

In still a further aspect of the present invention a stress-measuring system is presented, wherein the stress-measuring system, comprises the stress-measuring device, a skin conductance sensor for sensing the skin conductance of the user, and an output device for outputting the level of stress to the user.

In another further aspect of the present invention a stress-measuring method for determining a level of stress of a user, in particular long-term stress, is presented, the method comprising receiving a skin conductance signal indicating the skin conductance of the user, the skin conductance signal over time forming skin conductance trace data, and processing the skin conductance trace data, the processing comprising determining, over at least a portion of the skin conductance trace data, values of a rise time between at least two different points of the skin conductance trace data, determining a frequency distribution of the rise time values, and determining the level of stress of the user, in particular long-term stress, based on the determined frequency distribution.

In a still further aspect of the present invention a computer program is presented, wherein the computer program comprises program code means for causing a computer to carry out the steps of the stress-measuring method when said computer program is carried out on the computer.

The basic idea of the invention is to take the shape of the skin conductance trace into account by means of the rise time values (rise time between at least two different points, in particular exactly two points) and to use the frequency distribution of these rise time values to determine the stress level, in particular the long-term stress level. The rise time is basically a shape measure. Thus, the variety of shapes, or variety of rise time values, in the skin conductance trace data, in particular the skin conductance responses, are used to determine the long-term stress level of a user. It has been found that the type of the frequency distribution, in particular the shape of its histogram representation, is an indicator of the (chronically increased) blood pressure of the user (which is related to hypertension), and is thus also an indicator of the long-term stress level of the user. The level of long-term (or chronic) stress, thus the quantification of long-term stress, depends on conditions that change over a longer time period, for example a period of one or more weeks. According to this invention, a quantification of the cumulative effect of subsequent stressors, for example in a timeframe of several hours, is given. Using this invention, the long-term stress level (or allostatic load) can be assessed, and even a prediction of an altered stress response in the near future can be given after the occurrence of severe stressors. Also, the present invention provides a less obtrusive device, especially as it can be integrated into a wearable device, such as a wristband. Further, the hardware needed is inexpensive and can easily be miniaturized. Thus, also a less expensive device can be provided. Additionally, the present invention allows for a context independent stress measurement. Therefore, there is no need for additional contextual information, for example for user input, and thus a simple stress-measuring device and system can be provided that can measure stress throughout a day filled with daily life activities.

Preferred embodiments of the invention are defined in the dependent claims. It shall be understood that the claimed stress-measuring method, computer program, wearable device, and stress-measuring system has similar and/or identical preferred embodiments as the claimed stress-measuring device and as defined in the dependent claims.

In one embodiment, the stress-measuring device is adapted to extract the tonic component of the skin conductance signal or skin conductance trace data and to process the tonic component (as the skin conductance trace data). This can, for example, be performed by the processing unit. The tonic component indicates the gradual, long lasting changes of the skin conductance. The rise time values can then be determined in the tonic component, thus rises over a longer time span. These values, more particularly its frequency distribution, can then be used to determine the long-term stress level.

In an alternative or cumulative embodiment, the stress-measuring device is adapted to extract the phasic component of the skin conductance signal or skin conductance trace data and to process the phasic component (as the skin conductance trace data). The phasic component indicates the short term changes in the skin conductance. The rise time values can then be determined in the phasic component, thus rises over a shorter time span. These values, more particularly its frequency distribution, can then be used to determine the long-term stress level.

In an embodiment, the processing unit is adapted to detect peaks in the skin conductance trace data. In this way, the rise time values are only determined for the peaks (which are of interest) and not for the whole skin conductance trace data. For example, a value of the rise time for each (detected) peak can be determined. This reduces calculation time. This embodiment can for example be used in combination with the previous embodiments of separating and processing the tonic and/or phasic component.

In a variant of this embodiment, the peaks are detected using the slope of the skin conductance trace data. This provides for a more effective peak detection compared to a simple peak detection using only the amplitude.

In another variant of this embodiment, the processing unit is adapted to detect skin conductance responses as the peaks in the skin conductance data. This variant can for example be combined with the previous variant of detecting the slope of the skin conductance trace data. Also, this variant can for example be used in combination with the embodiment of separating and processing the phasic component of the skin conductance signal. In a variant of this variant, the processing unit is adapted to determine a value of the rise time for each (detected) skin conductance response. For example, an onset time point (time point where the skin conductance response starts) and a maximum time point (time point where the skin conductance response is at its maximum) are determined for each skin conductance response, and the value of the rise time is between the onset time point and its corresponding maximum time point. Thus, the rise time values are only determined for the skin conductance responses, which reduces calculation time and effort.

In a still further embodiment, the frequency distribution of the rise time values is determined using a histogram representation. This provides for an easy implementation.

In a further embodiment, the frequency distribution is a cumulative frequency distribution.

In another embodiment, the stress level is determined based on the uniformity or peakedness of the determined frequency distribution. In a variant of this embodiment, the stress level is higher when the determined frequency distribution is less uniform (or more peaked) and/or the stress level is lower when the determined frequency distribution is more uniform (or less peaked). This provides for a reliable way of determining the level of long-term stress. The uniformity/peakedness of the frequency distribution, or its histogram representation, is an indicator/estimator of the blood pressure, and thus also of the long-term stress level.

In a still further embodiment, the stress level is determined using at least one statistic measure selected from the group comprising the standard deviation, mean, variance, skewness and kurtosis of the determined frequency distribution. This enables to describe the type/shape of the frequency distribution (or its histogram representation) in a reliable manner.

In a variant of this embodiment, in particular in combination with the standard deviation as the statistic measure, the processing unit is adapted to determine an estimated (systolic) blood pressure value (of the user) based on the statistic measure, in particular the standard deviation. In particular the standard deviation is a good statistic measure to describe the type/shape of the frequency distribution (or its histogram representation), and to determine therefrom an indicator/estimator of the blood pressure of the user, and thus the long-term stress level. The (long-term) stress level of the user can then be determined according to the estimated blood pressure value. Thus, from the estimated (systolic) blood pressure value, or the estimated blood pressure values over time, the long-term stress level of the user/patient can be determined.

In a further variant, when the statistic measure is the standard deviation of the determined frequency distribution, the stress level is higher when the standard deviation is lower and/or the stress level is lower when the standard deviation is higher. In particular, when determining an estimated blood pressure value, the estimated blood pressure value is higher when the standard deviation is lower and/or the estimated blood pressure value is lower when the standard deviation is higher. Thus, there is a negative correlation between the estimated (systolic) blood pressure value (or long-term stress level) and the statistic measure of the determined frequency distribution, in particular the standard deviation. For a user/patient with hypertension and thus chronically increased blood pressure, his/her (systolic) blood pressure level will be at a high value for a longer period of time, in particular for a couple of hours, or days, or weeks.

In a still further embodiment, in particular in combination with or as an alternative to the previous embodiment, the stress level is determined by comparing the determined frequency distribution with at least one reference frequency distribution. For example, a functional distance is used to compare the determined frequency distribution with at least one reference frequency distribution. For example, the functional distance can be a divergence measure (such as Kullback-Leibler divergence). All these measures are good predictors for blood pressure, which is known to relate to long-term stress. Further, stress level could also be determined using other suitable ways, such as using suitably chosen quantiles or quantile ranges of the determined frequency distribution (or cumulative frequency distribution).

In a further embodiment, the stress-measuring device is adapted to form the skin conductance trace data over more than one hour, in particular more than 6 hours, more than 12 hours (half a day), more than 24 hours (one day), or even several days or weeks. This enables the determination of long-term stress which occurs over a longer time period.

In a variant of this embodiment, the processing unit is adapted to process the skin conductance trace data over more than one hour, in particular more than 6 hours, more than 12 hours (half a day), more than 24 hours (one day), or even several days or weeks. Thus, a large part or all of the formed skin conductance trace data (not only a small part) is processed in order to determine the long-term stress level.

BRIEF DESCRIPTION OF THE DRAWINGS

These and other aspects of the invention will be apparent from and elucidated with reference to the embodiment(s) described hereinafter. In the following drawings

FIGS. 6a and 6b show different exemplary histogram representations of frequency distributions.

DETAILED DESCRIPTION OF THE INVENTION

Figure 1:
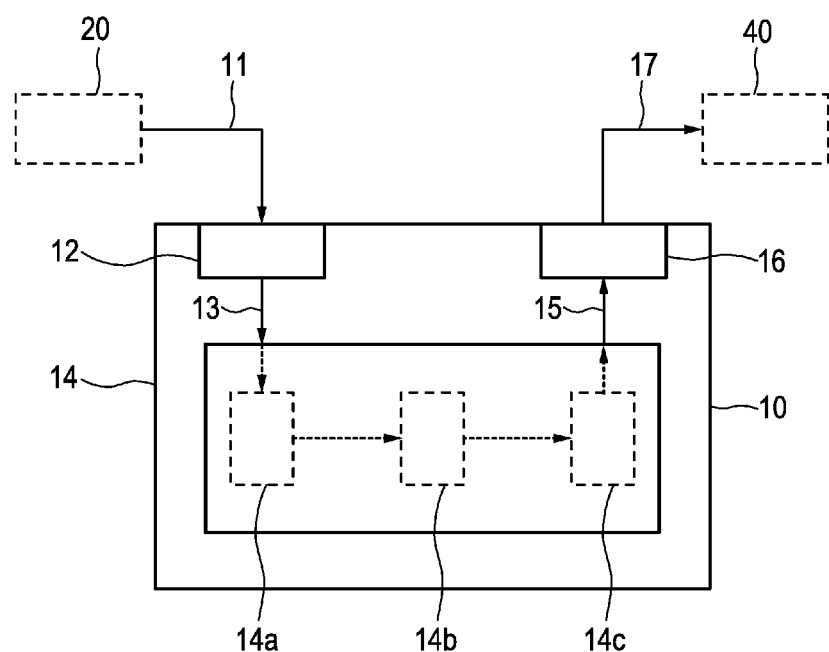
FIG. 1 shows a schematic diagram of a stress-measuring device according to an embodiment.

FIG. 1 shows a schematic diagram of a stress-measuring device 10 according to an embodiment, in particular a long-term stress measuring device. The stress-measuring device 10 comprises an input interface 12 for receiving a skin conductance signal 11 indicating the skin conductance of the user 1. For example, a skin conductance sensor 20 can sense the skin conductance of a user 1 and provide the corresponding skin conductance signal 11 to the input interface 12. The skin conductance signal 11 over time forms skin conductance trace data 13. For example, the stress-measuring device 10 can comprise a memory (not shown in FIG. 1) where the received skin conductance signal is stored over time to produce skin conductance trace data 13.

The stress-measuring device is in particular used to determine a level 15 of long-term stress (in the following simply referred to as stress level 15). Thus, the stress-measuring device 10 can be adapted to form the skin conductance trace data 13 over more than one hour, more than six hours, more than 12 hours (half a day), more than 24 hours (one day) or even several days or weeks. Thus, the memory described above must have enough capacity to store the skin conductance signal over this period of time.

The stress-measuring device 10 further comprises a processing unit 14 for processing the skin conductance trace data 13. The processing unit 14 is adapted to determine, over at least a portion of the skin conductance trace data 13, values of a rise time tr between at least two different points of the skin conductance trace data 13. This can, for example, be performed by first determination means 14a. Further, the processing unit 14 is adapted to determine the frequency distribution of the rise time tr values. This can, for example, be performed by second determination means 14b. Finally, the processing unit 14 is adapted to determine the level 15 of stress of the user 1 based on the determined frequency distribution. This can, for example, be performed by third determination means 14c. It will be understood that the described processing of the skin conductance trace data can be performed using any suitable hardware and/or software. For example the first, second and third determination means 14a, 14b, 14c can be implemented in software.

The stress-measuring device 10 of the embodiment in FIG. 1 further comprises an output interface 16 for outputting output data 17 indicating the stress level 15. For example, the output data 17 can be provided to an output device 40 for outputting the level 15 of stress to the user 1.

A corresponding stress-measuring method for determining a level 15 of stress of a user 1, in particular long-term stress, comprises receiving a skin conductance signal 11 indicating the skin conductance of the user 1, the skin conductance signal 11 over time forming skin conductance trace data 13, and processing the skin conductance trace data 13. The processing comprises determining, over at least a portion of the skin conductance trace data 13, values of a rise time between at least two different points of the skin conductance trace data 13, determining a frequency distribution of the rise time values, and determining the level 15 of stress of the user based on the determined frequency distribution. A computer program can be used, comprising program code means for causing a computer to carry out the steps of such a stress-measuring method when said computer program is carried out on the computer. The computer can be a personal computer or any other suitable computer means.

For example, an embedded processor can be used. The computer can be integrated into or be part of the stress-measuring device.

Figure 2:
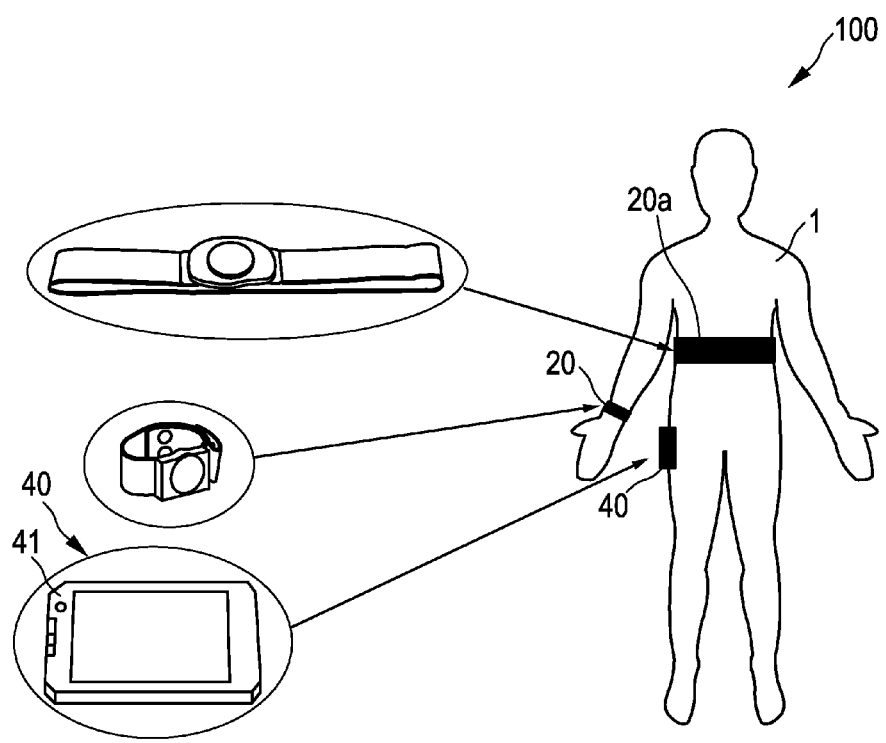
FIG. 2 shows an illustration of a stress-measuring system according to an embodiment.

FIG. 2 shows an illustration of a stress-measuring system 100 according to an embodiment. The stress-measuring system 100 comprises a skin conductance sensor 20 for sensing the skin conductance of the user 1. In FIG. 2, the skin conductance sensor 20 is integrated into a wearable device, wearable by the user 1, in particular a wristband. However, the skin conductance sensor 20 can also sense the skin conductance at other suitable body parts, such as the finger(s), and/or at the palmar or volar side of the hand. The stress-measuring system 100 further comprises an output device 40 for outputting the level 15 of stress to the user 1. The output device 40 can be portable, for example be clipped to a belt of the user 1 as indicated in FIG. 2. The output device 40 shown in FIG. 2 comprises display means 41 for displaying the stress level 15. Alternatively or additionally, the stress level 15 can also be output to the user 1 using sound, light, and/or vibration.

In general, the output device 40 can be a separate device (as shown in FIG. 2), or it can be integrated into for example the skin conductance sensor 20 or a wearable device comprising the sensor. The output can be through a variety of modalities such as audio (e.g. sound), visual (e.g. light), and/or haptic (e.g. vibration) feedback.

The stress-measuring system 100 further comprises the stress-measuring device 10 previously described. The stress-measuring device 10 can be a separate part, or can be integrated into the wearable device or into the output device 40. Also, the stress-measuring device 10 can be adapted to output a warning signal, when the stress level 15 exceeds a predefined threshold. The output device 40 can be adapted to output a warning to the user when receiving the warning signal. In this way, the device and system can be used in an application to prevent people with high risk of e.g. brain injury, such as stroke patients, from getting too tense and thereby getting high blood pressure leading to potential brain injury. The stress-measuring system 100 can further comprise additional devices, such as an electrocardiogram (ECG) sensor, like the ECG chest belt 20a shown in FIG. 2. The ECG sensor can sense the electrocardiogram of the user 1. From the electrocardiogram the heart rate variability (HRV) can be determined, which is also known to relate to stress. In this way, the determination of the stress level 15 as explained above can be further enriched. In general, the long-term measurement of stress can be combined with other measurements of stress (potentially short(er) term stress) to obtain richer information on the stress level or state of the user. This additional measurement of (short-term) stress can for example be obtained by physiological measurements, such as the ECG mentioned above. However, also other suitable measurements such as BVP, respiration, skin temperature, electroencephalography (EEG)/brain activity, activity measurement (e.g. through an accelerometer) and/or questionnaires can be used for additional measurements.

Figure 3:
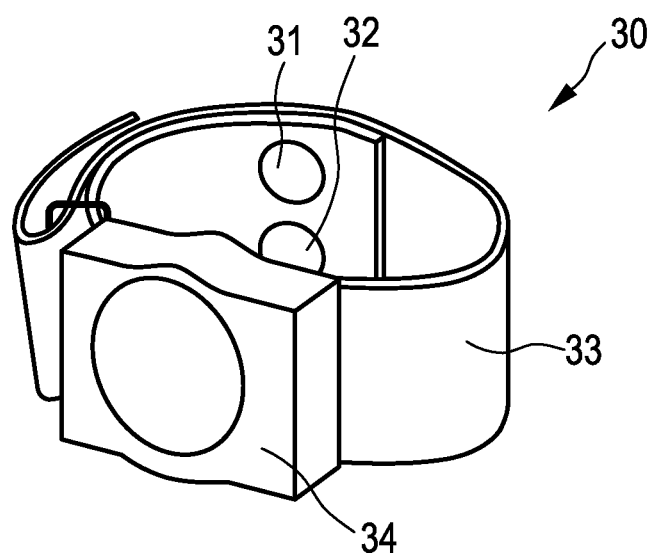
FIG. 3 shows a perspective view of a wearable device according to an embodiment.

FIG. 3 shows a perspective view of an embodiment of a wearable device 30 wearable by a user. In the embodiment of FIG. 3, the wearable device 30 is in form of a wristband comprising a wristband material part 33 and a casing 34. It will be understood that the wearable device 30 could also be worn around any other suitable body part, such as the ankle, foot or hand. In FIG. 3, two skin conductance electrodes 31, 32 are integrated into the wrist band material 33. The skin conductance electrodes 31, 32 are used for sensing the skin conductance of the user. Thus, the wearable device 30 comprises the skin conductance sensor 20. In particular, the skin conductance electrodes 31, 32 can be arranged so as to contact the volar side of the wrist where there is normally not a lot of hair. Thus, a better measurement of the skin conductance can be provided.

Further, the wearable device 30 comprises the stress-measuring device 10, for example the stress-measuring device 10 described with reference to FIG. 1. The stress-measuring device 10 can be integrated into the casing 34 of the wearable device 30. The wearable device 30 can further comprise a transmitter for wirelessly transmitting data over a wireless communication link, such as the output data 17.

Figure 4:
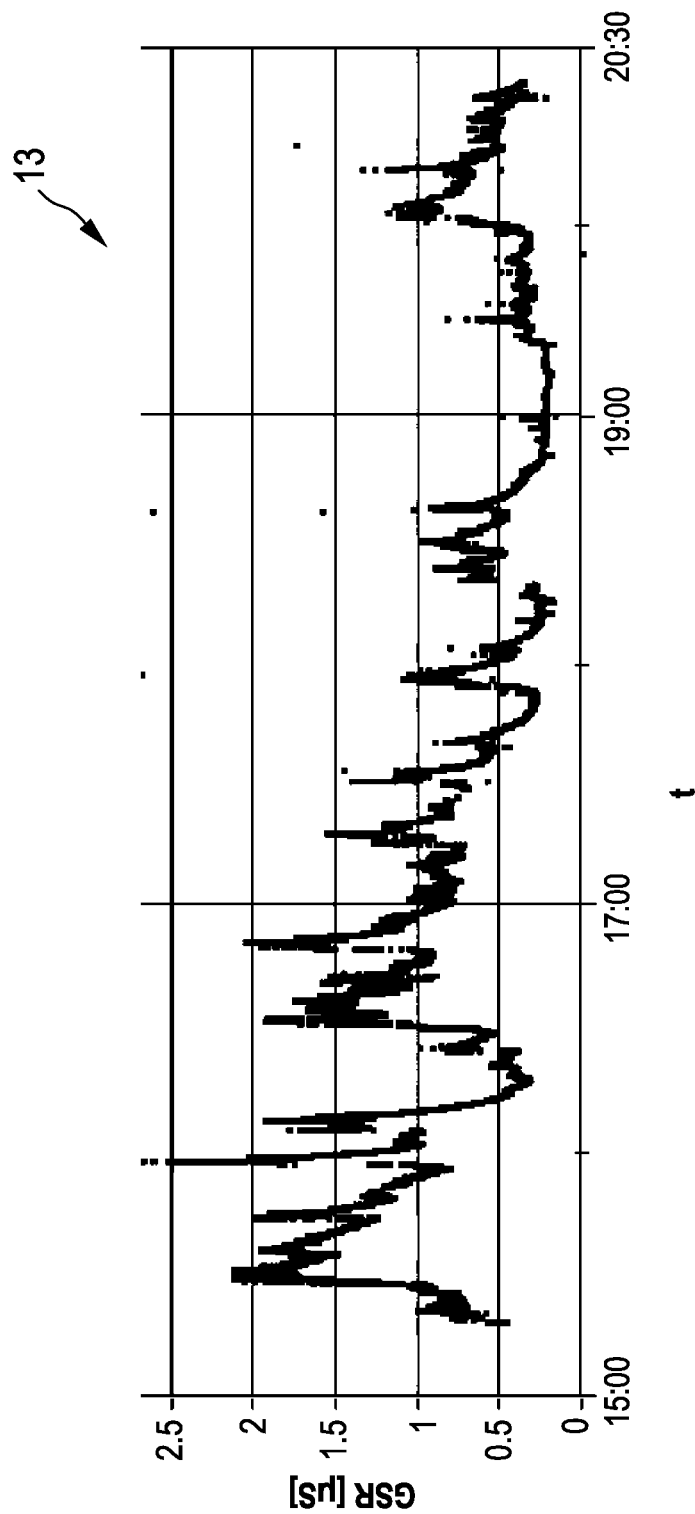
FIG. 4 shows a diagram of exemplary skin conductance trace data.

FIG. 4 shows a diagram of an exemplary skin conductance trace data 13, for example measured with the wearable device 30 as shown in FIG. 3. The x-axis denotes the time t over a period of several hours, here about 5½ hours, from 15:00 o'clock (3 p.m.) to 20:30 o'clock (8:30 p.m.). Thus, the skin conductance data 13 is formed over several hours. The processing unit 14 can then in particular be adapted to process the skin conductance trace data 13 over several hours.

In FIG. 4, the y-axis denotes the skin conductance, also called galvanic skin response (GSR), measured in micro-Siemens µS. Each point of the skin conductance trace data 13 indicates the skin conductance sensed by the skin conductance sensor 20 at that specific point in time t. Emotional events show as peaks with a steeper rising slope and a more gentle down slope. In FIG. 4, each peak corresponds to the response of the sympathetic nervous system to an emotionally arousing event (communicated via the vagus nerve to the sweat glands of the skin).

In particular, the skin conductance trace data 13 comprises or is the tonic component. The tonic component indicates the gradual, long lasting changes of the skin conductance, thus it is represented by the general or basic form of the skin conductance trace shown in FIG. 4. The stress-measuring device 10, as for example shown in FIG. 1, can be adapted to extract the tonic component of the skin conductance signal 11 (before the skin conductance trace data 13 is formed), thus the skin conductance trace data 13 only comprises (or is) the tonic component (not the phasic component), and then the tonic component is processed by the processing unit 14. Alternatively, the stress-measuring device 10 can be adapted to extract the tonic component of the skin conductance trace data 13 (after the skin conductance trace data 13 is formed), and then the tonic component of the skin conductance trace data is processed by the processing unit 14. For example, from the skin conductance trace data 13 shown in FIG. 4, the tonic component can be extracted and processed. The rise time tr values can then be determined in the tonic component, thus rises over a longer time span. The tonic component can be extracted by, for example, using a frequency filter, such as a low-pass filter, for example for frequencies up to 0.05 Hz.

Alternatively or cumulatively, the skin conductance trace data 13 can comprise or be the phasic component. The phasic component indicates the short term changes in the skin conductance, thus it would be represented by the small changes superimposed on the general/basic (tonic) form of the skin conductance trace, for example the thickness of the line (or wobbles) shown in FIG. 4. The stress-measuring device 10, as for example shown in FIG. 1, can be adapted to extract the phasic component of the skin conductance signal 11 (before the skin conductance trace data 13 is formed), thus the skin conductance trace data 13 only comprises (or is) the phasic component (not the tonic component), and then the phasic component is processed by the processing unit 14. Alternatively, the stress-measuring device 10 can be adapted to extract the phasic component of the skin conductance trace data 13 (after the skin conductance trace data 13 is formed), and then the phasic component of the skin conductance trace data is processed by the processing unit 14. For example, from the skin conductance trace data 13 shown in FIG. 4, the phasic component can be extracted and processed. The rise time tr values can then be determined in the phasic component, thus rises over a shorter time span. The phasic component can be extracted by, for example, using a frequency filter, such as a high-pass filter, for example for frequencies of more than 0.05 Hz. For example, also a method for detecting skin conductance responses can be used (such as e.g. a method known as SCRGAUGE, see Kolish P., 1992, "SCRGAUGE—A Computer Program for the Detection and Quantification of SCRs", Electrodermal Activity, Boucsein, W. ed., New York: Plenum: 432-442, which is incorporated herein by reference), as will be explained in the following.

Figure 5:
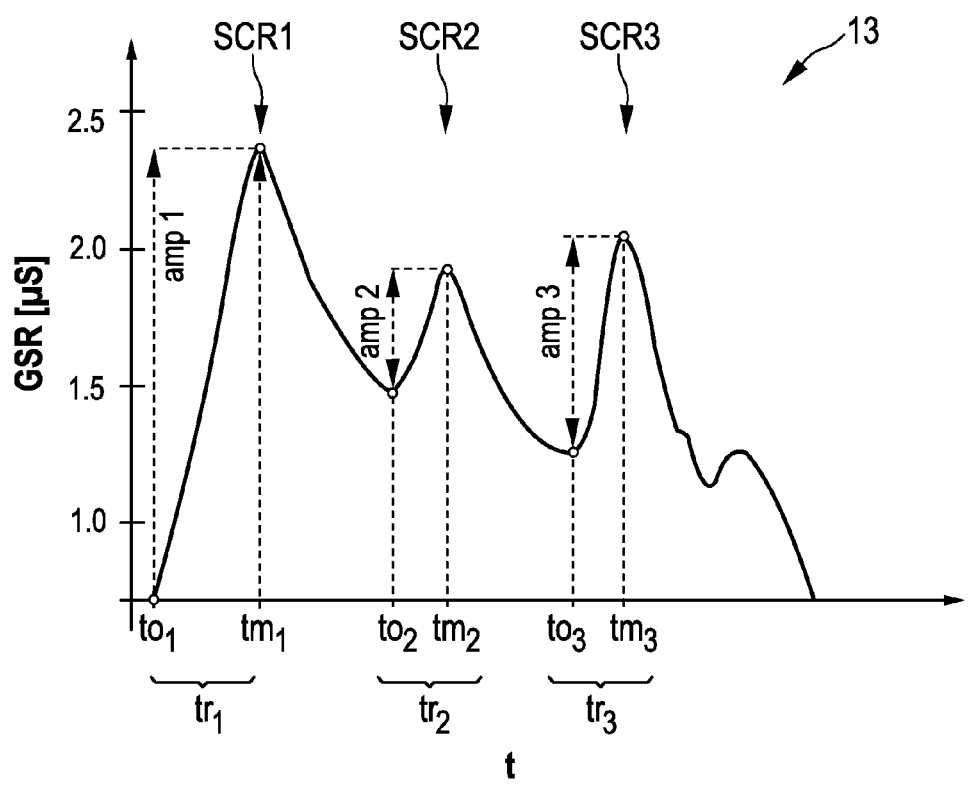
FIG. 5 shows an enlarged portion of the exemplary skin conductance trace data of FIG. 4.

FIG. 5 shows an enlarged portion of the exemplary skin conductance trace data 13 of FIG. 4, for example a couple of minutes (e.g. about 3 minutes) of the skin conductance trace data 13 shown in FIG. 4. The processing unit 12 is adapted to detect peaks in the skin conductance trace data 13 of FIG. 5. In particular, the processing unit 12 is adapted to detect skin conductance responses SCR 1, SCR2, SCR3 (see FIG. 5) as peaks in the skin conductance trace data 13. For example, the skin conductance responses SCR 1, SCR2, SCR3 are detected using the slope of the skin conductance trace data 13. The skin conductance responses SCR are detected by evaluating the slope, or gradient of incline, at subsequent points of the skin conductance trace data 13. If the slope exceeds a given value, it is determined that a skin conductance response SCR is present. Then, an onset time point $to_1$, $to_2$, $to_3$ (time point where the SCR starts) and a maximum time point $tm_1$, $tm_2$, $tm_3$ (time point where the SCR is at its maximum) are determined for each skin conductance response SCR1, SCR2, SCR3. Detection of the onset time point to of a skin conductance response SCR is performed by moving backwards in the curve to the point of maximal curvature. The detection of the maximum time point tm of a skin conductance response SCR is performed by moving forward until the slope becomes negative. Then, the value of the rise time $tr_1$, $tr_2$, $tr_3$ is determined between the (each) onset time point $to_1$, $to_2$, $to_3$ and its corresponding maximum time point $tm_1$, $tm_2$, $tm_3$. Thus, referring to FIG. 5, a value of the rise time tr for each detected skin conductance response SCR1, SCR2, SCR3 is determined. For each skin conductance response SCR1, SCR2, SCR3 the value of the rise time $tr_1$, $tr_2$, $tr_3$ is between the (exactly) two different points $to_1$, $to_2$, $to_3$ (onset time point) and $tm_1$, $tm_2$, $tm_3$ (maximum time point), respectively.

Additionally, also other values for each skin conductance response can be determined. In one example, the amplitude (amplitude change) amp1, amp2, amp3 can be additionally determined. In particular, the amplitude amp1, amp2, amp3 corresponding to the respective rise time $tr_1$, $tr_2$, $tr_3$ can be determined, for example between the (each) onset time point $to_1$, $to_2$, $to_3$ and its corresponding maximum time point $tm_1$, $tm_2$, $tm_3$. In another example, also the half-recovery time $t_{rec}/2$ can be additionally determined, at a point where the skin conductance trace data falls below ½ of the amplitude of the skin conductance response SCR1, SCR2, SCR3. In case, the skin conductance trace data does not fall to this value within a reasonable amount of time, the half-recovery time $t_{rec}/2$ can be estimated by means of extrapolation of the skin conductance trace with negative slope that occurs just after the local maximum.

Next, the frequency distribution of these determined values of the rise time tr is determined, in particular using a histogram representation. FIG. 6a and FIG. 6b show two different exemplary histogram representations of such frequency distributions. The x-axis denotes the rise time tr and the y-axis denotes the frequency. Alternatively, the y-axis could also denote the cumulative frequency, in which case the frequency distribution would be a cumulative frequency distribution. For example, more than 100, in particular more than 400 or more than 800, peaks or skin conductance responses can be used for the frequency distribution or histogram representation. The histogram representation can for example be normalized.

Then, the level 15 of stress of the user 1 is determined based on the determined frequency distribution or its histogram representation. In particular, the stress level 15 can be determined based on the uniformity or peakedness of the determined frequency distribution or histogram representation. For example, it is determined that the stress level 15 is higher, when the determined frequency distribution or histogram representation is less uniform (or more peaked). Similarly, it is determined that the stress level 15 is lower, when the determine frequency distribution or histogram representation is more uniform (or less peaked). As can be seen in FIG. 6a, the frequency distribution or histogram representation is less uniform. Thus, in this case, it is determined that the stress level 15 is higher. As can be seen in FIG. 6b, the frequency distribution or histogram representation is more uniform. Thus, it is determined that the stress level 15 is lower. Consequently, the uniformity or shape of the frequency distribution or histogram representation can be used to determine the long-term stress level 15.

The stress level 15 can be determined using at least one statistic measure selected from the group comprising the standard deviation, mean, variance, skewness and kurtosis of the determined frequency distribution or its histogram representation. In particular, the stress level 15 can be determined using the standard deviation std of the determined frequency distribution or its histogram representation. Having n values $x_i$, $i=1, 2, \ldots n$, the standard deviation std is $$std = \sqrt{\frac{1}{n-1} \sum_{i=1}^{n} (x_i - m)^2},$$

$$m = \frac{1}{n} \sum_{i=1}^{n} x_i$$

In a computational representation, the standard deviation is $std = SQRT(1/(n-1)SUM((x-m)^2)) = SQRT(1/(n-1)(n*m^2 + SUM(x^2) - 2*m*SUM(x))$. This only requires the administration of the number of values n, the sum values SUM(x) and the square sum of values $SUM(x^2)$. Thus, only little computational power is required to administer this statistic measure over a longer time period.

It has been found that these statistic measures, in particular the standard deviation of the frequency distribution or the histogram representation, are a good indicator of the blood pressure, which is known to be related to long-term stress. In particular when the statistic measure is the standard deviation of the determined frequency distribution, the stress level is higher when the standard deviation is lower and/or the stress level is lower when the standard deviation is higher.

The processing unit 14 can be adapted to determine an estimated (in particular systolic) blood pressure value based on the statistic measure, in particular the standard deviation. The (long-term) stress level of the user can then be determined according to the estimated blood pressure value. Thus, from the estimated (systolic) blood pressure value, or the estimated blood pressure values over time, the long-term stress level of the user/patient can be determined.

The estimated blood pressure value is higher when the standard deviation is lower and/or the estimated blood pressure value is lower when the standard deviation is higher. Thus, there is a negative correlation between the estimated (systolic) blood pressure value (or long-term stress level) and the statistic measure of the determined frequency distribution, in particular the standard deviation. This will be explained in the following.

Figure 7:
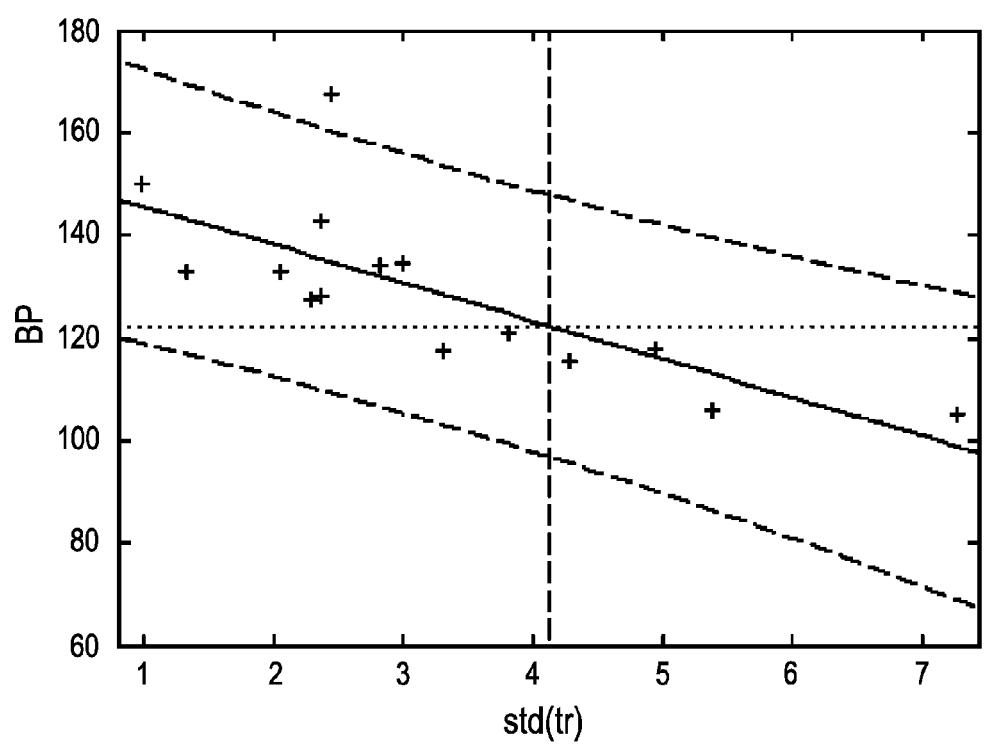
FIG. 7 shows a diagram of an exemplary linear regressor.

FIG. 7 shows a diagram of an exemplary linear regressor. The x-axis denotes the standard deviation std of the frequency distribution of the rise time tr values. The y-axis denotes the systolic blood pressure BP. The solid line represents the linear regressor of the estimated blood pressure BP for a given measurement of std(tr): BP=a+std*b. The correlation of the example shown in FIG. 7 is −0.75, which is considered to be very high in the context of physiological measurements. Therefore, the standard deviation std(tr) can be considered as a good indicator for systolic blood pressure. The linear regressor of the estimated blood pressure BP declines with increasing std(tr) indicating that higher measured std values correspond to lower blood pressure values (as also indicated by the negative correlation).

To specify the accuracy of the linear regressor, the plus signs in FIG. 7 indicate measurement values based on skin conductance measurements and simultaneous systolic blood pressure measurements for different patients. The dashed lines in FIG. 7 indicates a confidence bound around the linear regressor line (solid line), here indicating a 95% confidence interval around the linear regressor, thus the area in which 95% of the estimated blood pressure values are expected to occur (for each possible value of std(tr)). It should be noted that the confidence range highly depends on the number of measurements. Thus, generally speaking, the estimated (in particular systolic) blood pressure is determined with a certain confidence range, for example with a probability of more than 80%, in particular more than 90%, in particular more than 95%.

In the example shown in FIG. 7, the estimated blood pressure values are calculated over a time period of approximately three hours, for example using the skin conductance trace data of FIG. 4 and/or the histogram representations of FIG. 6a and FIG. 6b. It is important to note that by using such a long time period, in which a wide variety of tasks can be performed by the user, the skin conductance trace data 13, or the determined skin conductance responses or peaks, include a wide range of contextual effects, reflecting daily life well. Thus, it is shown that the statistic measure of the standard deviation of the values of the rise time is fairly context-independent. Therefore, this statistic measure is well suitable for the case in which people wear a stress-measurement device for a longer time period in daily life, in which many different context situations influence their skin conductance.

Alternatively or cumulatively, the stress level 15 can be determined by comparing the determined frequency distribution with at least one reference frequency distribution, in particular a set of reference frequency distributions. For example, a functional distance can be used to compare the determined frequency distribution with at least one reference frequency distribution. In one example, the functional distance is a divergence measure (such as Kullback-Leibler divergence). For example, a reference frequency distribution or histogram can be used for each class of stress level (or blood-pressure level). Once a new measurement has been made, the similarity between the new frequency distribution or histogram representation and each of the reference frequency distributions can be calculated using the divergence measure. Then, the closest reference frequency distribution is determined and its corresponding stress level/estimated blood-pressure value is determined. This method requires the formulation of at least one, in particular a set of, reference frequency distributions, which is a one-time action and can be predefined, e.g. hard coded into the device. The formulation of the reference frequency distributions(s) could be automated through machine learning that incorporates the same similarity measure (e.g. a divergence measure). For example, the reference frequency distributions can be learned through "learning vector quantization".

Thus, the comparison of the determined frequency distribution with at least one reference frequency distribution can comprise one or more of the following steps:

creating (at one time, before the comparison is started) the at least one reference frequency distribution (in particular at least two reference frequency distributions), for example one reference frequency distribution per blood-pressure class (e.g. BP-classes: {0-70, 71-100, 101-130, 131-Inf}), for every determination of the (long-term) stress level or estimated blood pressure value, compare the determined frequency distribution (or its histogram representation) with each of the reference distribution(s), in particular by calculating and using the functional distance between them (e.g. provided by divergence measure)

for every determination of the (long-term) stress level or blood pressure estimate, choose the closest reference frequency distribution by choosing the reference frequency distribution with the smallest divergence measure value.

Additionally, the corresponding (long-term) stress level or estimated blood pressure value (blood pressure (BP) label) can be output (e.g. 71-100).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A stress-measuring device for determining a level of stress of a user, the device comprising:
    an input interface configured to receive a skin conductance signal indicating a skin conductance of the user, the skin conductance signal over time forming skin conductance trace data, and
    a processor configured to:
        process the skin conductance trace data,
        detect peaks in the skin conductance trace data,
        calculate slope values preceding the skin conductance peaks,
        categorize peaks as skin conductance responses when the slope values of the peaks exceed a given value, and
        determine rise times for each skin conductance response (SCR), and
    wherein the processor is further configured to determine:
        a frequency distribution of the rise time (tr) values,
        a standard deviation of the frequency distribution, and
        the level of stress of the user based on the determined standard deviation.

2. The stress-measuring device of claim 1, wherein the processor is configured to extract the tonic component of the skin conductance signal or the skin conductance trace data and to process the tonic component and/or configured to extract the phasic component of the skin conductance signal or the skin conductance trace data and to process the phasic component.

3. The stress-measuring device of claim 1, wherein the processor is configured to determine the frequency distribution of the rise time values using a histogram representation.

4. The stress-measuring device of claim 1, wherein the processor is configured to determine the stress level based on the uniformity or peakedness of the determined frequency distribution.

5. The stress-measuring device of claim 4, wherein the stress level is higher when the determined frequency distribution is less uniform and/or wherein the stress level is lower when the determined frequency distribution is more uniform.

6. The. stress-measuring device of claim 1, wherein the processor is configured to determine the stress level using at least one statistic measure selected from the group comprising the variance, skewness and kurtosis of the determined frequency distribution.

7. The stress-measuring device of claim 6, wherein the processor is configured to determine an estimated blood pressure value based on the at least one statistic measure.

8. The stress-measuring device of claim 1, wherein the processor is configured to determine the stress level by comparing the determined frequency distribution with at least one reference frequency distribution.

9. A wearable device wearable by a user, the wearable device comprising the stress-measuring device of claim 1, and a skin conductance sensor configured to sense the skin conductance of the user.

10. A stress-measuring system, comprising:
    the stress-measuring device of claim 1, and
    a skin conductance sensor configured to sense the skin conductance of the user;
    wherein the processor is further configured to control a display device to output the level of stress to the user.

11. The stress-measuring device of claim 1, wherein the processor is further configured to determine the stress level using the variance, skewness and kurtosis of the determined frequency distribution.

12. The stress-measuring device of claim 1, further comprising a low-pass filter configured to extract the tonic component of the skin conductance signal.

13. A stress-measuring system comprising:
    the stress-measuring device of claim 1; and
    a stress output device configured to output an audio warning signal if the stress level exceeds a predefined threshold.

14. A stress-measuring method for determining a level of stress of a user, the method comprising:
    with one or more processors, receiving a skin conductance signal indicating a skin conductance of the user, the skin conductance signal over time forming skin conductance trace data,
    with the one or more processors:
        detect peaks in the skin conductance trace data,
        calculate slope values preceding the skin conductance peaks,
        categorize peaks as skin conductance responses when the slope values of the peaks exceed a given value, and
        determine rise times for each skin conductance response (SCR), and
    with the one or more processors, determining:
        a frequency distribution of the rise time (tr) values,
        a standard deviation of the frequency distribution, and
        the level of stress of the user based on the determined standard deviation.

15. A non-transitory computer-readable medium carrying program code for causing a computer to carry out the steps of the stress-measuring method as claimed in claim 14.

16. A blood pressure measuring device comprising:
    one or more processors configured to:
        receive a skin conductance signal indicating a skin conductance of the user, the skin conductance signal over time forming skin conductance trace data,
        detect peaks in the skin conductance trace data,
        calculate slope values preceding the skin conductance peaks,
        categorize peaks as skin conductance responses when the slope values of the peaks exceed a given value, and
        determine rise times for each skin conductance response (SCR), and
        determine a frequency distribution of the rise time (tr) values, to determine at least one statistic measure of the determined frequency distribution, and to determine an estimated blood pressure value based on the statistic measure, and
    an output device configured to:
        display the estimated blood pressure value, and
        output an audio warning signal if a stress level related to the blood pressure value exceeds a predefined threshold.

17. The blood pressure measuring device of claim 16, wherein the statistic measure is a standard deviation.

18. A method of transforming a skin conductance signal into an estimated blood pressure value comprising:
    with one or more computer processors, receiving the skin conductance signal indicating a skin conductance of the user, the skin conductance signal over time forming skin conductance trace data, and with the one or more computer processors:
- detect peaks in the skin conductance trace data,
- calculate slope values preceding the skin conductance peaks,
- categorize peaks as skin conductance responses when the slope values of the peaks exceed a given value, and
- determine rise times for each skin conductance response (SCR), and with the one or more computer processors, determining a frequency distribution of the rise time (tr) values to determine at least one statistic measure of the determined frequency distribution and to determine the estimated blood pressure value based on the statistic measure.

\* \* \* \* \*